US009855085B2

(12) United States Patent
Ferro et al.

(10) Patent No.: US 9,855,085 B2
(45) Date of Patent: Jan. 2, 2018

(54) BONE CEMENT APPLICATOR

(71) Applicant: AOD Holdings, LLC, Arroyo Grande, CA (US)

(72) Inventors: Thomas D. Ferro, Arroyo Grande, CA (US); Austin T. Ferro, Arroyo Grande, CA (US); Scott Gill, Arroyo Grande, CA (US); Joe Phillips, Arroyo Grande, CA (US); Donald Lee, Arroyo Grande, CA (US); John Park, Arroyo Grande, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 637 days.

(21) Appl. No.: 14/316,813

(22) Filed: Jun. 27, 2014

(65) Prior Publication Data

US 2015/0005778 A1 Jan. 1, 2015

Related U.S. Application Data

(60) Provisional application No. 61/841,131, filed on Jun. 28, 2013, provisional application No. 62/003,970, filed on May 28, 2014.

(51) Int. Cl.
A61B 17/56 (2006.01)
A61B 17/60 (2006.01)
A61F 2/00 (2006.01)
A61B 17/88 (2006.01)

(52) U.S. Cl.
CPC .................. *A61B 17/8802* (2013.01)

(58) Field of Classification Search
None
See application file for complete search history.

(56) References Cited

U.S. PATENT DOCUMENTS

2010/0262245 A1* 10/2010 Alfaro .................. A61F 2/4465
623/17.16

* cited by examiner

*Primary Examiner* — Sameh Boles
(74) *Attorney, Agent, or Firm* — McDonnell Boehnen Hulbert & Berghoff LLP

(57) ABSTRACT

A bone cement applicator for applying a bone cement to a bone surface is provided. The bone cement applicator includes a bone cement receiver, a first housing and a second housing. The bone cement receiver has a first opening to be connected with a bone cement supplier supplying the bone cement. The first housing is connected with the bone cement receiver. The second housing is connected with the first housing. A cavity is formed between the first housing and the second housing. The cavity is in fluid communication with the first opening. The second housing includes a contact surface and a plurality of holes. The contact surface is in contact with the bone surface. The holes are located on the contact surface, in which the bone cement reaches the bone surface after sequentially flowing through the first opening, the cavity, and the holes.

21 Claims, 15 Drawing Sheets

US 9,855,085 B2

BONE CEMENT APPLICATOR

RELATED APPLICATIONS

This application claims priority to U.S. Provisional Application No. 61/841,131, filed Jun. 28, 2013, and U.S. Provisional Application No. 62/003,970, filed May 28, 2014, which are herein incorporated by references.

BACKGROUND

Technical Field

The present disclosure relates to bone cement applicators. More particularly, the present disclosure relates to bone cement applicators for tibias or femurs.

Description of Related Art

Arthroplasty procedures can be used to repair damaged joints. During an arthroplasty procedure, an arthritic or dysfunctional joint can be remodeled or realigned, or an implant can be placed into the damage joint. Arthroplasty procedures can be performed in different regions of the body, such as a knee, a hip, a shoulder, or an elbow.

A specific type of arthroplasty procedure is a total knee arthroplasty (TKA), where a damaged knee joint is replaced with prosthetic implants. During a TKA procedure, the damaged portion of the distal region of the femur may be removed and replaced with a metal shell and the proximal region of the tibia may be removed and replaced with a polymer plastic and a metal stem.

Currently, the total knee arthroplasty often utilizes bone cement to adhere the implant onto the bone. In general, the bone cement consists of a powder of polymethyl methacrylate (PMMA) and a liquid of methylmethacrylate (MMA). When the PMMA and MMA are mixed in a rough ratio of 2:1, a bone cement of polymethyl methacrylate forms. The moment the PMMA and MMA come into contact, polymerization begins. For instance, in a matter of 7-15 minutes, the bone cement sets and completely hardens. Depending on preference, the surgeons apply bone cement early, when the bone cement is less viscous and liquid-like, or late, when the bone cement is more viscous and putty like. Working with a less viscous bone cement is advantageous because it allows the bone cement to permeate deeper into the resected bone, which provides fixation that is anchored deeper into the bone. However, the application of a less viscous bone cement is much more difficult. The surgeons have very little time to apply the bone cement in a uniform manner within the small time frame when the bone cement is at its optimum consistency, or less viscous. Therefore, there is a need in the field for a bone cement applicator to improve the efficiency of applying the bone cement to a patient.

SUMMARY

A technical aspect of the present disclosure provides a bone cement applicator which can increase the efficiency of applying bone cement onto the bone surface as required, making the process quick and easy.

According to an embodiment of the present disclosure, a bone cement applicator for applying a bone cement to a bone surface is provided. The bone cement applicator includes a bone cement receiver, a first housing and a second housing. The bone cement receiver has a first opening to be connected with a bone cement supplier supplying the bone cement. The first housing is connected with the bone cement receiver. The second housing is connected with the first housing. A cavity is formed between the first housing and the second housing. The cavity is in fluid communication with the first opening. The second housing includes a contact surface and a plurality of holes. The contact surface is in contact with the bone surface. The holes are located on the contact surface and in fluid communication with the cavity, in which the bone cement reaches the bone surface after sequentially flowing through the first opening, the cavity, and the holes.

In one or more embodiments of the present disclosure, the contact surface includes a first zone and a second zone. The second zone surrounds at least a part of a peripheral edge of the first zone. The holes include a first set of holes and a second set of holes respectively located in the first zone and the second zone, in which a cross-sectional area parallel with the contact surface of each of the second set of holes is larger than a cross-sectional area parallel with the contact surface of each of the first set of holes.

In one or more embodiments of the present disclosure, the first housing has a second opening in fluid communication between the first opening and the cavity, and an orthographic projection of the second opening on the contact surface at least partially overlaps with the first zone.

In one or more embodiments of the present disclosure, the second housing is a porous structure.

In one or more embodiments of the present disclosure, the second housing is an open-celled foam.

In one or more embodiments of the present disclosure, the bone cement applicator is made of plastic.

In one or more embodiments of the present disclosure, the bone cement receiver includes a receiver surface. The first opening is located on the receiver surface and the receiver surface forms an angle with the contact surface.

In one or more embodiments of the present disclosure, the first housing has a second opening in fluid communication between the first opening and the cavity, and the bone cement receiver is rotatably engaged with the second opening.

In one or more embodiments of the present disclosure, the bone cement receiver includes a threaded portion located at an inner wall of the first opening and configured to be detachably engaged with the bone cement supplier.

In one or more embodiments of the present disclosure, bone cement applicator further includes a ratchet clip connected to an end of the bone cement receiver away from the first housing for fastening the bone cement supplier.

In one or more embodiments of the present disclosure, the first housing has a second opening and at least one intermediate channel. The second opening is in fluid communication with the first opening. The intermediate channel is in fluid communication between the second opening and the cavity. An orthographic projection of the intermediate channel on the contact surface extends away from an orthographic projection of the second opening on the contact surface.

In one or more embodiments of the present disclosure, the second housing has a plurality of indentations located on the contact surface, and each of the holes is in fluid communication with the corresponding indentation.

In one or more embodiments of the present disclosure, each of the indentations is shaped as a hexagonal column.

In one or more embodiments of the present disclosure, the first housing has a pair of first extending portions connected with each other and extending away from the second opening. The second housing has a pair of second extending portions connected with each other. Each of the first extending portions is connected with the corresponding second extending portion, and an accommodation space is formed between the first extending portions and between the second extending portions, such that a tibial eminence where a pair of bi-cruciate ligaments is located can be accommodated in the accommodation space.

In one or more embodiments of the present disclosure, each of the first extending portions has a proximal end proximal to the second opening and a distal end distal to the second opening, and perpendicular distances of a top surface of each of the first extending portions relative to the contact surface decrease gradually from the proximal end towards the distal end.

In one or more embodiments of the present disclosure, the bone cement receiver is connected with the proximal ends.

In one or more embodiments of the present disclosure, the bone cement applicator further includes a pair of compression blocks, and each of the compression blocks is located on the corresponding top surface, configured to be pressed by a pressing tool.

In one or more embodiments of the present disclosure, the bone cement receiver includes a receiver surface. The first opening is located on the receiver surface. The bone cement applicator further includes a rotatable connector connected with the first housing and rotatably connected with the bone cement receiver, such that an angle between the receiver surface and the contact surface can be adjusted.

According to another embodiment of the present disclosure, a bone cement applicator for applying a bone cement to a bone surface is provided. The bone cement applicator includes a bone cement receiver and a housing. The bone cement receiver has a first opening configured to be connected with a bone cement supplier supplying the bone cement. The housing is connected with the bone cement receiver and has a cavity. The housing includes a contact surface, a second opening and at least one intermediate channel. The contact surface forms a peripheral edge for the cavity in contact with the bone surface. The second opening is in fluid communication with the first opening. The intermediate channel is in fluid communication between the second opening and the cavity, in which an orthographic projection of the intermediate channel on the bone surface extends away from an orthographic projection of the second opening on the bone surface.

In one or more embodiments of the present disclosure, the housing further includes at least one protruding part disposed on the contact surface for engaging the bone surface.

In one or more embodiments of the present disclosure, the contact surface has a plurality of contact sub-surfaces, and at least two adjacent ones of the contact sub-surfaces form an angle.

In one or more embodiments of the present disclosure, the housing includes a male portion and a female portion. The male portion has a male joint. The female portion has a female joint. The male joint is detachably engaged with the female joint.

In one or more embodiments of the present disclosure, the male portion has a male surface and the female portion has a female surface. The male joint is a guiding piece and the female joint is a guiding slot. The guiding piece and the guiding slot are slidably connected, such that a distance between the male surface and the female surface can be adjusted.

When compared with the prior art, the embodiments of the present disclosure mentioned above have at least the following advantages:

(1) In the embodiments of the present disclosure, a cavity is formed between the first housing and the second housing and the bone cement reaches the bone surface after sequentially flowing through the first opening, the cavity, and the holes. In this way, the bone cement will fill up the cavity before extruding out of each of the holes and this helps to promote a more even pressurized exit of the bone cement that is being extruded. Moreover, the holes of the second housing can help spreading out the bone cement over the bone surface.

(2) In the embodiments of the present disclosure, the contact surface of the second housing includes the first zone and the second zone, and the cross-sectional area parallel with the contact surface of each of the second set of holes located in the second zone is larger than the cross-sectional area parallel with the contact surface of each of the first set of holes located in the first zone. Therefore, when the bone cement reaches the cavity, the bone cement will get accumulated in the first zone and will be spread out to the second zone. Thus, the advantage of viscosity of the bone cement is positively utilized. In this way, the effectiveness of the spreading out of the bone cement over the bone surface before passing though the holes onto the bone surface is enhanced.

(3) In the embodiments of the present disclosure, the bone cement flows onto the bone surface through the holes. In this way, the region of the bone surface receiving the bone cement is restricted by the location of the holes. Therefore, the risk that the bone cement flows to an undesired region is avoided.

(4) In the embodiments of the present disclosure, the first opening is located on the receiver surface of the bone cement receiver and the receiver surface forms an angle with the contact surface. In this way, the hone cement supplier can be connected with the bone cement receiver in an appropriate orientation convenient for the surgeon.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
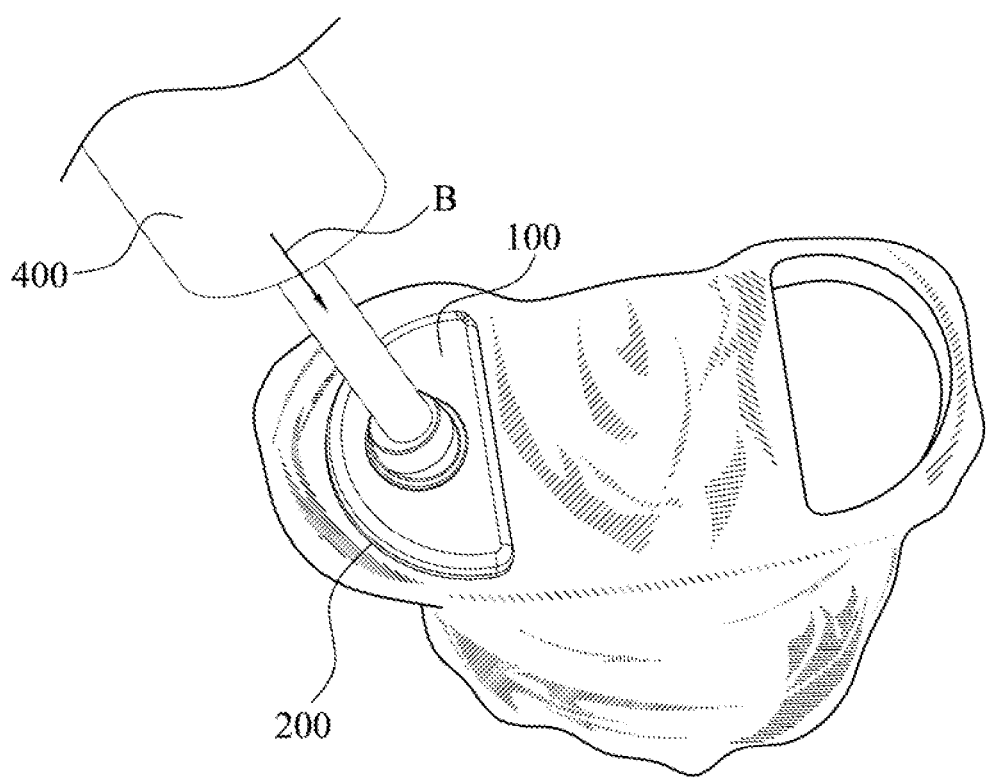
FIG. 1 is a schematic diagram of a bone cement applicator according to an embodiment of the present disclosure, illustrating the scenario the bone cement applicator is located on a bone surface and a bone cement supplier is supplying a bone cement into the bone cement applicator.

Drawings will be used below to disclose a plurality of embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
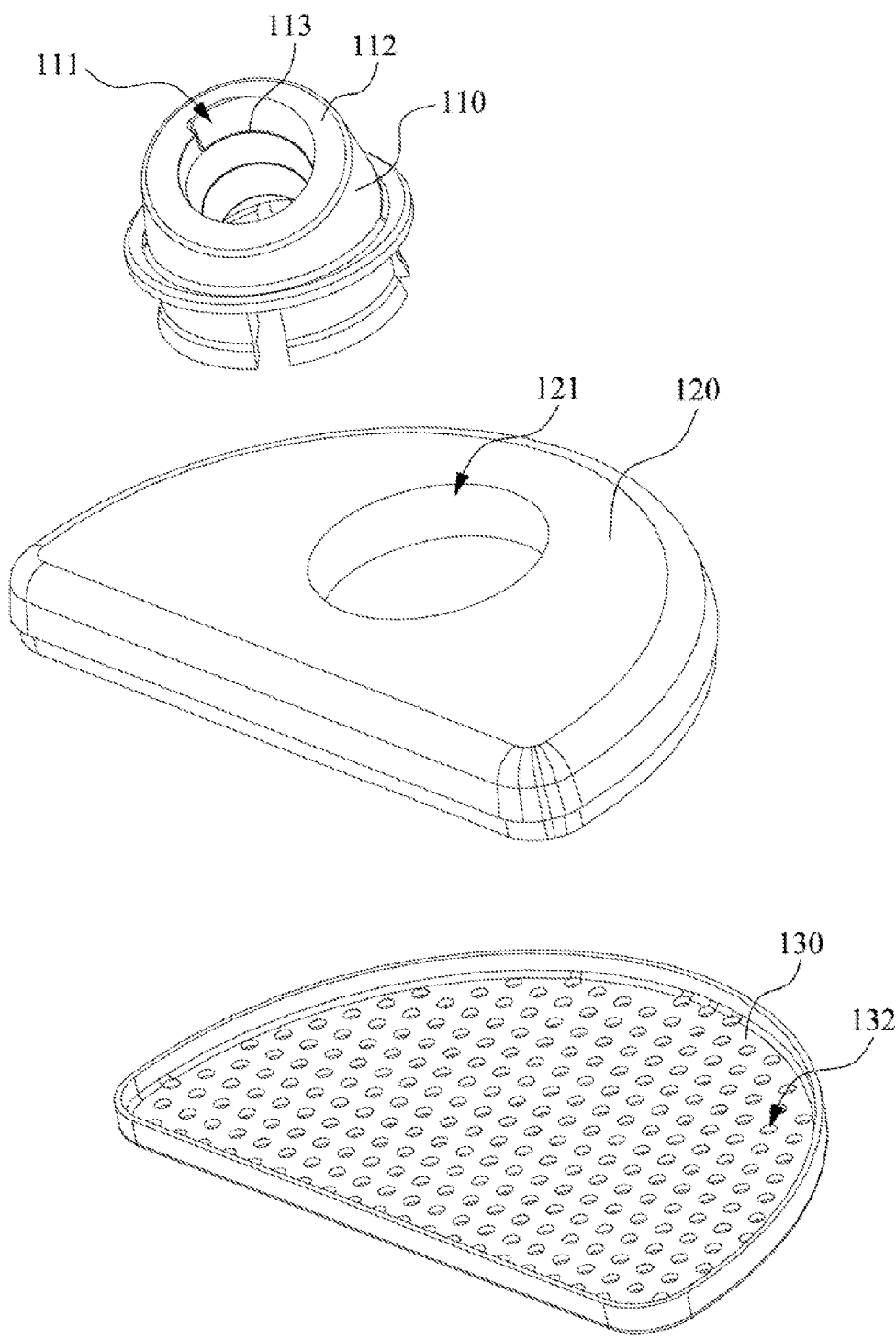
FIG. 2 is an exploded perspective view of the bone cement applicator of FIG. 1.
Figure 3:
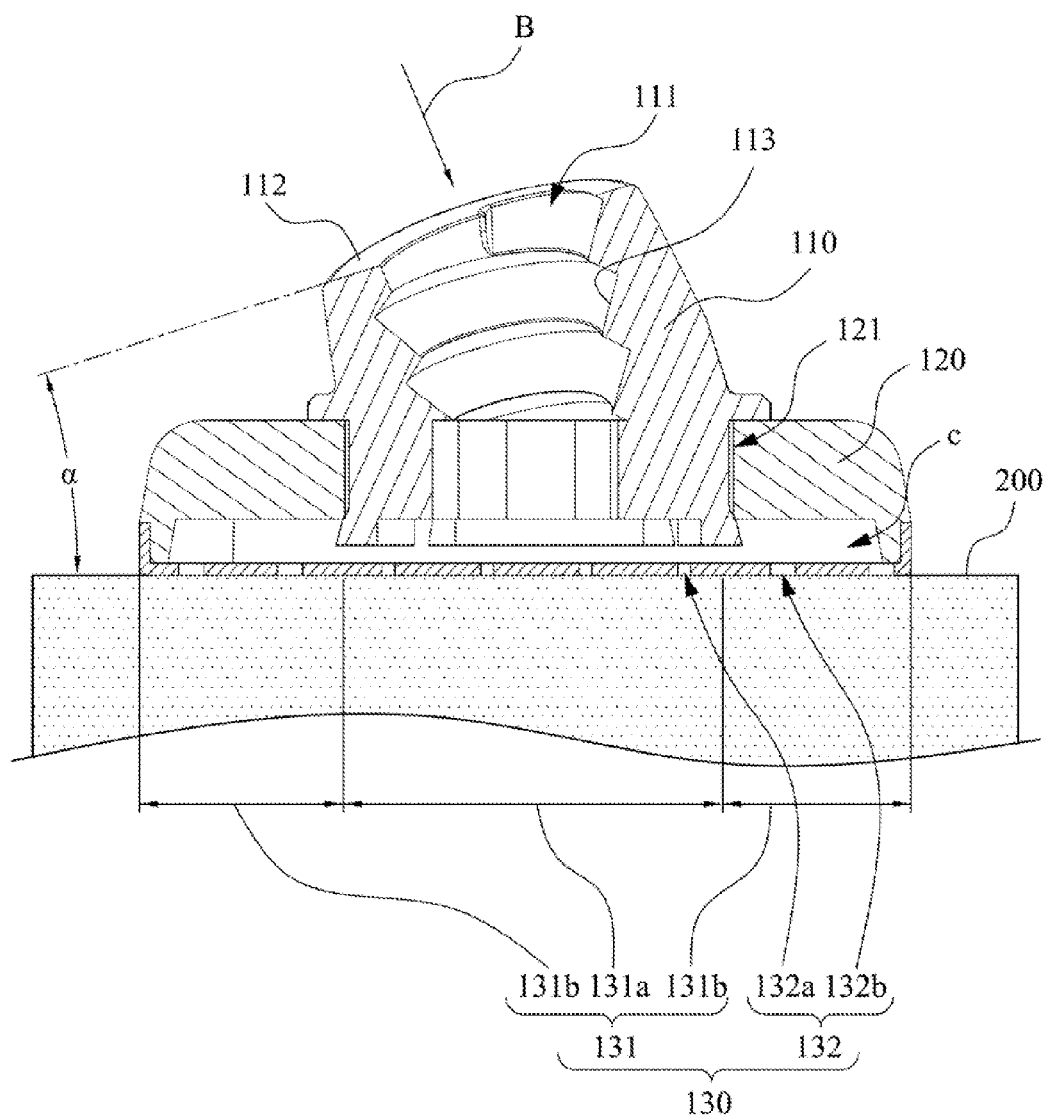
FIG. 3 is a sectional view of the bone cement applicator of FIG. 1.

FIG. 1 is a schematic diagram of a bone cement applicator 100 according to an embodiment of the present disclosure, illustrating the scenario the bone cement applicator 100 is located on a bone surface 200 and a bone cement supplier 400 is supplying a bone cement B into the bone cement applicator 100. FIG. 2 is an exploded perspective view of the bone cement applicator 100 of FIG. 1. FIG. 3 is a sectional view of the bone cement applicator 100 of FIG. 1. As shown in FIGS. 1-3, the bone cement applicator 100 for applying the bone cement B to the bone surface 200 of a tibia or a femur is provided. The bone cement applicator 100 includes a bone cement receiver 110, a first housing 120 and a second housing 130. The bone cement receiver 110 has a first opening 111 to be connected with a bone cement supplier 400 supplying the bone cement B. The first housing 120 is connected with the bone cement receiver 110. The second housing 130 is connected with the first housing 120. A cavity C is formed between the first housing 120 and the second housing 130. The cavity C is in fluid communication with the first opening 111. The second housing 130 includes a contact surface 131 and a plurality of holes 132. The contact surface 131 is in contact with the bone surface 200. The holes 132 are located on the contact surface 131 and in fluid communication with the cavity C, in which the bone cement B reaches the bone surface 200 after sequentially flowing through the first opening 111, the cavity C, and the holes 132.

To be more specific, when the bone cement B is supplied to the cavity C through the first opening 111, the bone cement B will fill up the cavity C before extruding out of each of the holes 132. This helps to promote a more even pressurized exit of the bone cement B that is being extruded. Moreover, the holes 132 of the second housing 130 can help spreading out the bone cement B over the bone surface 200.

In addition, since the bone cement B flows on to the bone surface 200 through the holes 132, the region of the bone surface 200 receiving the bone cement B is restricted by the location of the holes 132. Therefore, the risk that the bone cement B flows to an undesired region is avoided.

In the aspect of material, the bone cement applicator 100 can be made of plastic. To be more specific, the part of the second housing 130 in contact with the bone surface 200 can be silicone. However, these choices of material do not limit the present disclosure.

Figure 4:
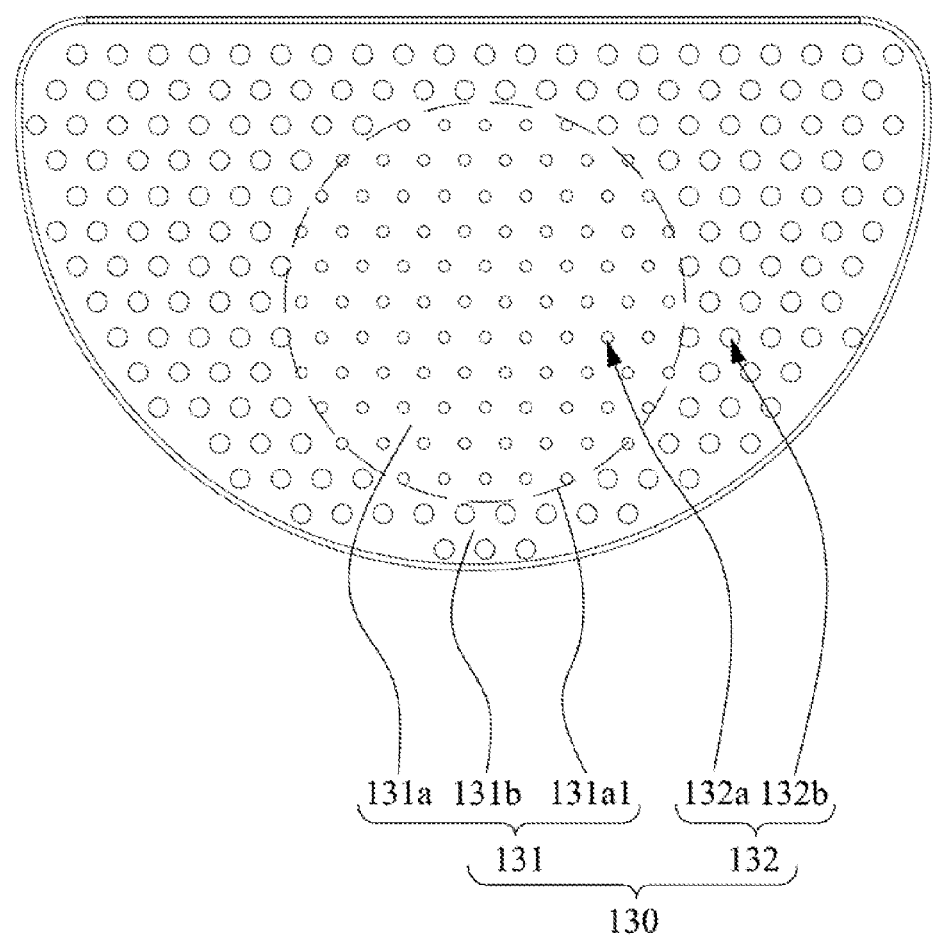
FIG. 4 is a bottom view of the bone cement applicator of FIG. 1.

FIG. 4 is a bottom view of the bone cement applicator 100 of FIG. 1. As shown in FIG. 4, the contact surface 131 of the second housing 130 includes a first zone 131a and a second zone 131b. The second zone 131b surrounds the first zone 131a, or at least a part of a peripheral edge 131a1 of the first zone 131a. The holes 132 include a first set of holes 132a and a second set of holes 132b respectively located in the first zone 131a and the second zone 131b, in which the cross-sectional area parallel with the contact surface 131 of each of the second set of holes 132b is larger than the cross-sectional area parallel with the contact surface 131 of each of the first set of holes 132a. This means, relative to the second set of holes 132b, the flowing of bone cement B through the first set of holes 132a is more difficult. Therefore, when the bone cement B reaches the cavity C, the bone cement B will flow through the first set of holes 132a in a relatively slower manner.

To be more specific, as shown in FIGS. 2-3, the first housing 120 has a second opening 121 in fluid communication between the first opening 111 and the cavity C, and an orthographic projection of the second opening 121 on the contact surface 131 at least partially overlaps with the first zone 131a. This means when the bone cement B reaches the cavity C, at least some of the bone cement B will fall on the first zone 131a first. Therefore, since the bone cement B flows through the first set of holes 132a located in the first zone 131a in a relatively slower manner, the bone cement B will get accumulated and will be spread out to the second zone 131b where the second set of holes 132b are located. Thus, the advantage of viscosity of the bone cement B is positively utilized. In this way, the effectiveness of the spreading out of the bone cement B over the bone surface 200 before passing though the holes 132 onto the bone surface 200 is enhanced. In practice, the contact surface 131 can be divided into more than two zones with different sizes of holes 132, such that the sizes of the holes 132 increase gradually towards the edge of the contact surface 131. However, this arrangement of holes 132 on the contact surface 131 does not limit the present disclosure.

In the practical application, the second housing 130 is a porous structure. On the other hand, the second housing 130 can also be an open-celled foam, provided that the bone cement B can flow through the holes 132 from the cavity C onto the bone surface 200.

Moreover, the bone cement receiver 110 includes a receiver surface 112. The first opening 111 is located on the receiver surface 112 and the receiver surface 112 forms an angle α with the contact surface 131. As a result, the bone cement supplier 400 can be connected with the bone cement receiver 110 in an appropriate orientation convenient for the surgeon.

In addition, to further increase the flexibility when the surgeon adjusts the orientation of the bone cement supplier 400 during operation, the bone cement receiver 110 is rotatably engaged with the second opening 121.

As shown in FIGS. 2-3, the bone cement receiver 110 includes a threaded portion 113 located at an inner wall of the first opening 111. The threaded portion 113 is configured to be detachably engaged with the bone cement supplier 400 (shown in FIG. 1) such that the connection of the bone cement supplier 400 with the bone cement applicator 100 can be secured. Consequently, the surgeon can exert a pressure manually to the bone cement applicator 100 through the bone cement supplier 400 in order to hold the bone cement applicator 100 in position.

Figure 5:
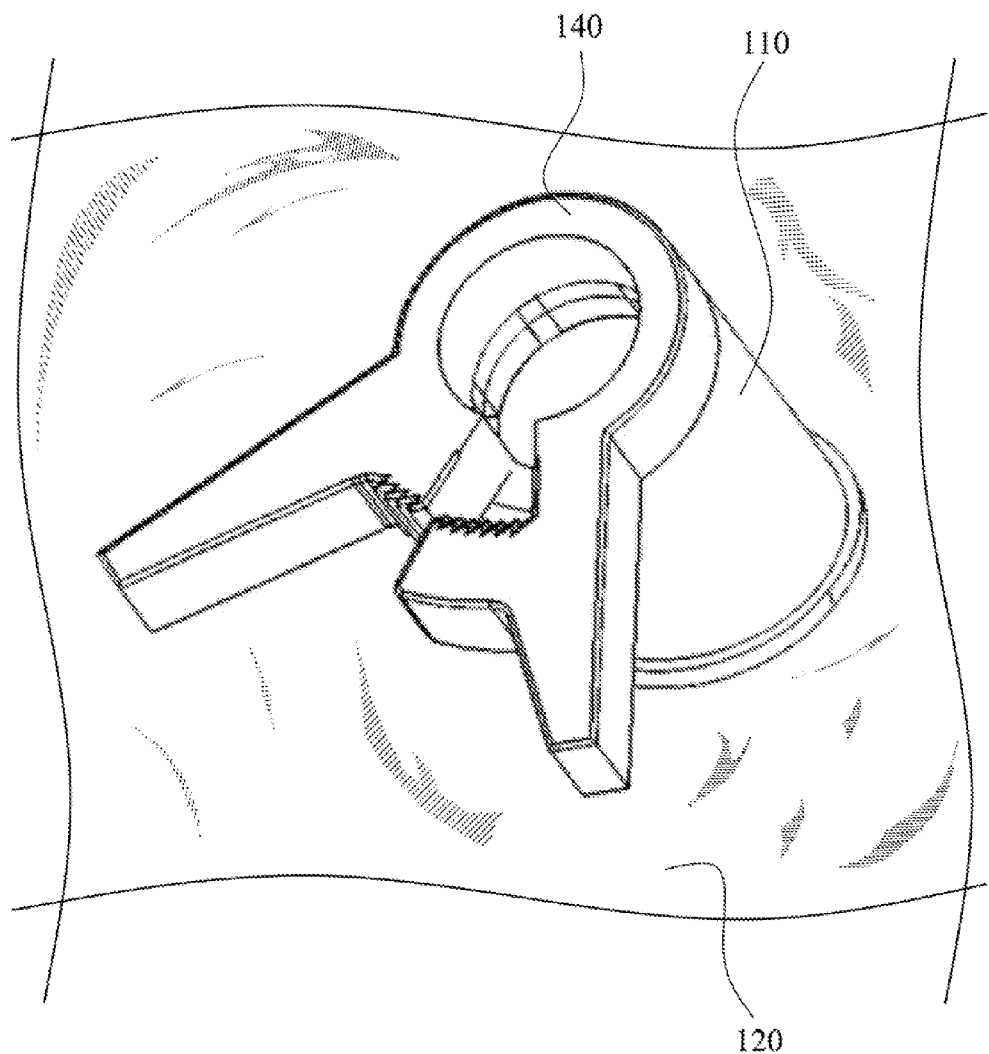
FIG. 5 is a partial perspective diagram of a bone cement applicator according to another embodiment of the present disclosure, in which a ratchet clip is connected to an end of the bone cement receiver.

FIG. 5 is a partial perspective diagram of a bone cement applicator 100 according to another embodiment of the present disclosure, in which a ratchet clip 140 is connected to an end of the bone cement receiver 110. As shown in FIG. 5, the ratchet clip 140 is connected to the end of the bone cement receiver 110 away from the first housing 120, for fastening the bone cement supplier 400 (shown in FIG. 1). With the ratchet clip 140 connected to the bone cement receiver 110, the connection of the bone cement supplier 400 with the bone cement applicator 100 can be further secured.

Figure 6:
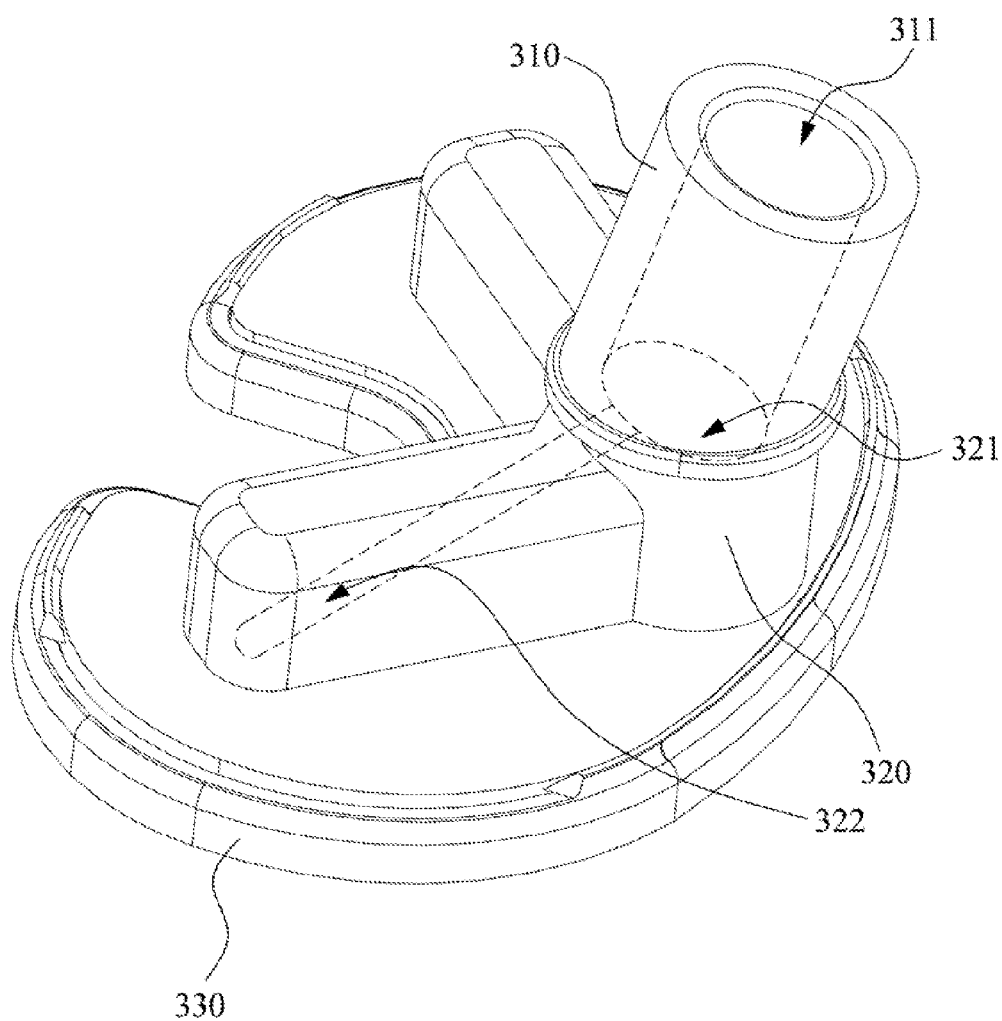
FIG. 6 is a perspective view of a bone cement applicator according to a further embodiment of the present disclosure.
Figure 7:
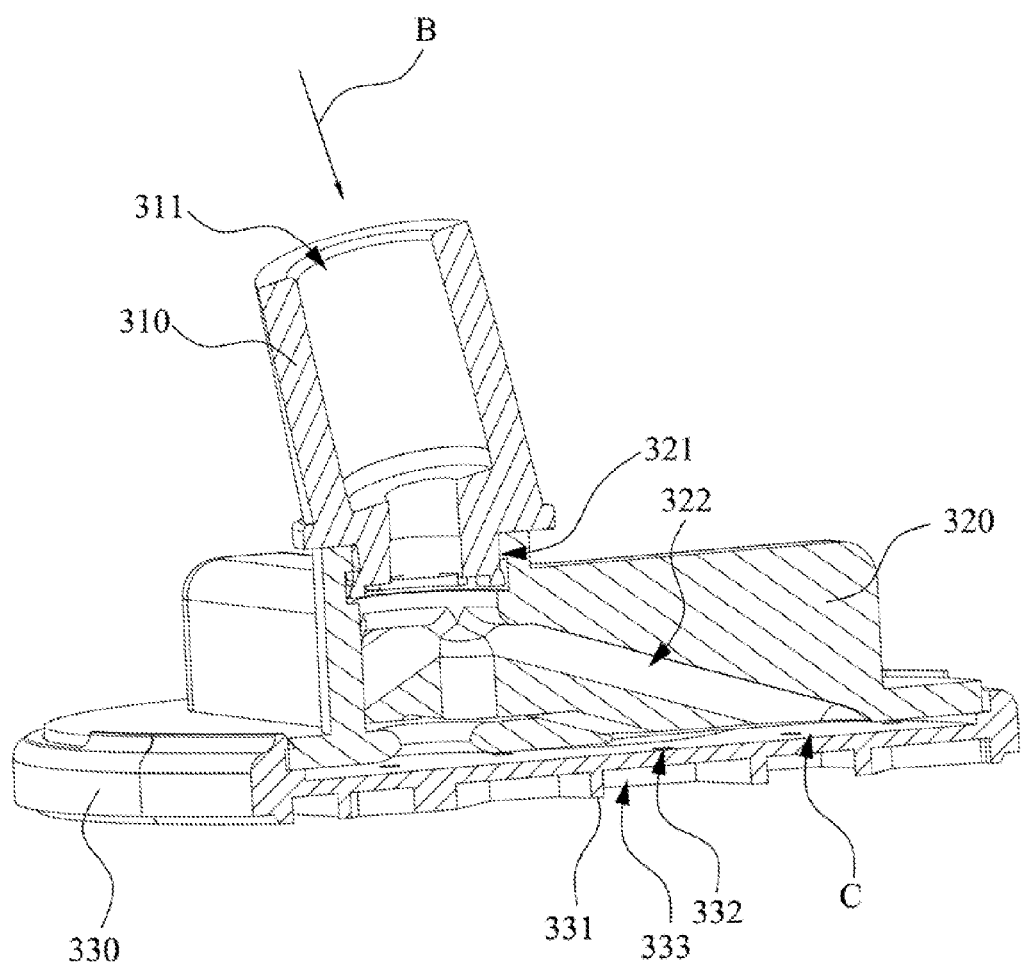
FIG. 7 is a sectional view of the bone cement applicator of FIG. 6.

FIG. 6 is a perspective view of a bone cement applicator 300 according to a further embodiment of the present disclosure. FIG. 7 is a sectional view of the bone cement applicator 300 of FIG. 6. As shown in FIGS. 6-7, the first housing 320 has a second opening 321 and at least one intermediate channel 322. The second opening 321 is in fluid communication with the first opening 311 of the bone cement receiver 310. The intermediate channel 322 is in fluid communication between the second opening 321 and the cavity C. Consequently, an orthographic projection of the intermediate channel 322 on the contact surface 331 of the second housing 330 extends away from an orthographic projection of the second opening 321 on the contact surface 331. In this way, the bone cement B can be directed by the intermediate channel 322 to a desired location other than the region of the contact surface 331 on where the orthographic projection of the second opening 321 falls.

Figure 8:
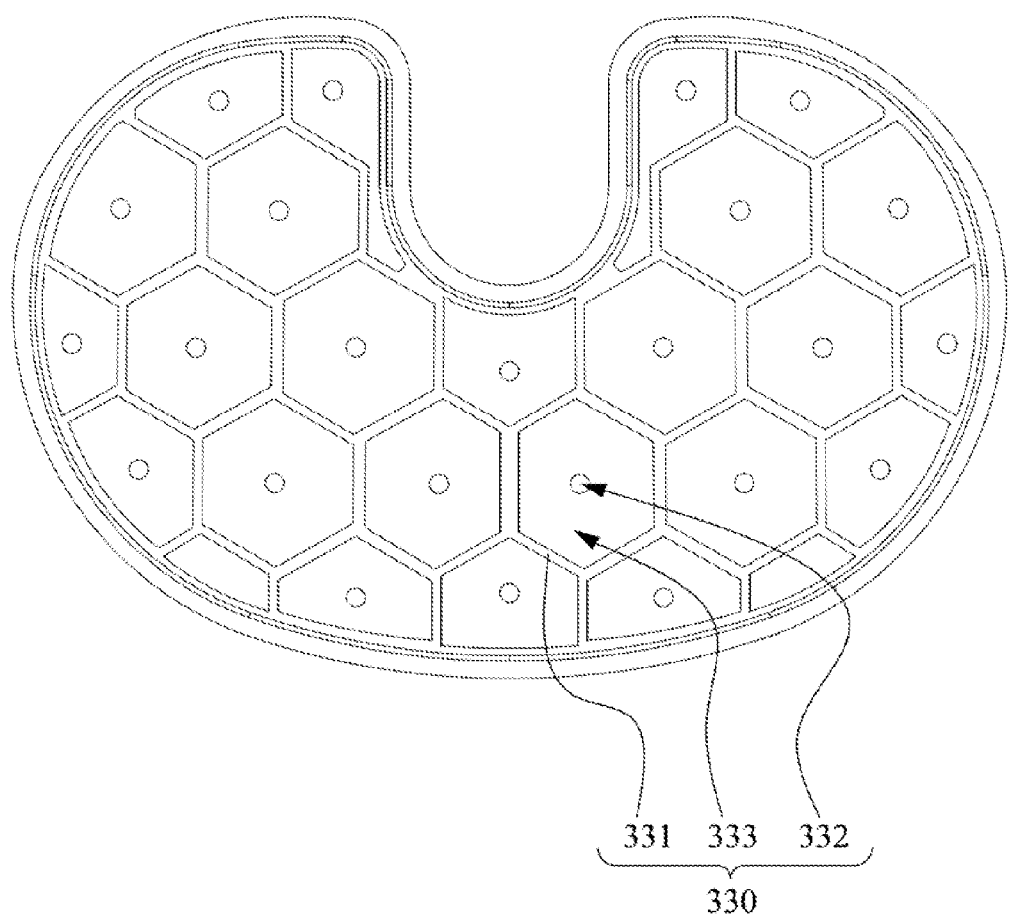
FIG. 8 is a bottom view of the hone cement applicator of FIG. 6.

FIG. 8 is a bottom view of the bone cement applicator 300 of FIG. 6. As shown in FIGS. 7-8, the second housing 330 has a plurality of indentations 333 located on the contact surface 331, and each of the holes 332 is in fluid communication with the corresponding indentation 333. When the bone cement B is applied, the bone cement B will fill up each of the indentations 333. Thus, the pressure of the bone cement B acting on the bone surface 200 can be more or less equalized among the indentations 333. In this embodiment, each of the indentations 333 is shaped as a hexagonal column. However, this shape of the indentation 333 does not limit the present disclosure.

Figure 9:
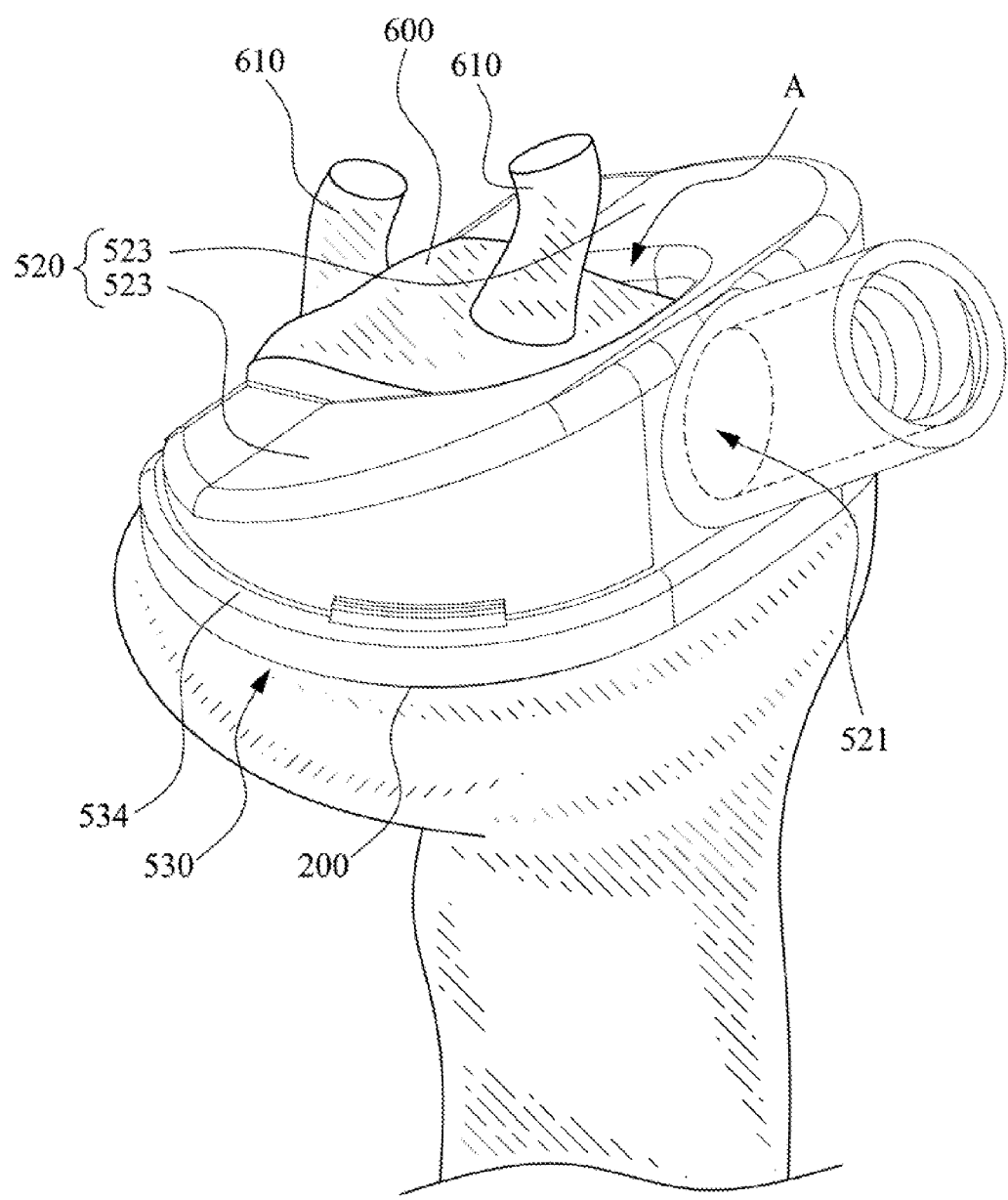
FIG. 9 is a schematic diagram of a bone cement applicator according to another embodiment of the present disclosure, in which a tibial eminence where a pair of bi-cruciate ligaments are located is accommodated.
Figure 10:
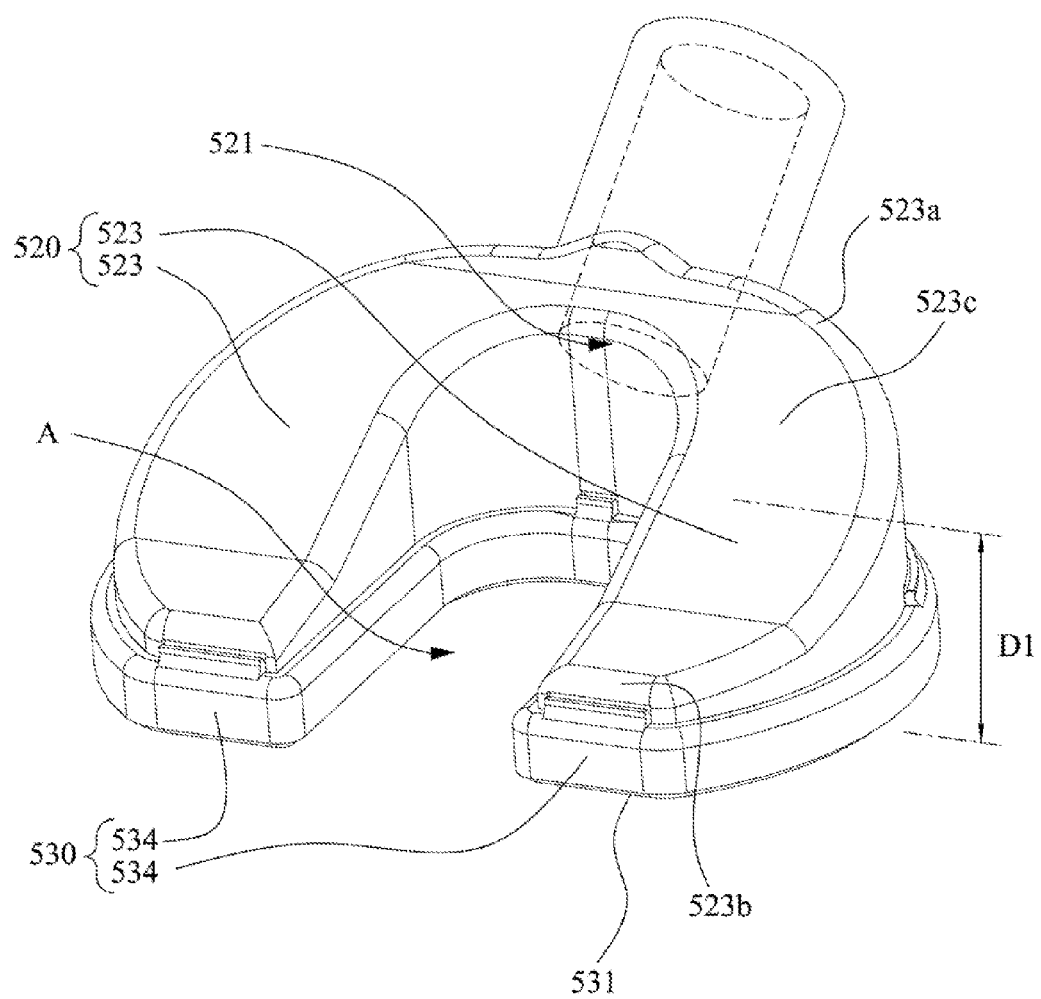
FIG. 10 is a perspective view of the bone cement applicator of FIG. 9.

FIG. 9 is a schematic diagram of a bone cement applicator 500 according to another embodiment of the present disclosure, in which a tibial eminence 600 where a pair of bi-cruciate ligaments 610 is located is accommodated. FIG. 10 is a perspective view of the bone cement applicator 500 of FIG. 9. As shown in FIGS. 9-10, the first housing 520 has a pair of first extending portions 523 connected with each other and extending away from the second opening 521. The second housing 530 has a pair of second extending portions 534 connected with each other. Each of the first extending portions 523 is connected with the corresponding second extending portion 534, and an accommodation space A is formed between the first extending portions 523 and between the second extending portions 534, such that the tibial eminence 600 where the pair of bi-cruciate ligaments 610 is located can be accommodated in the accommodation space A.

The bi-cruciate ligament 610 includes the anterior cruciate ligament (ACL) and the posterior cruciate ligament (PCL). In other words, when both the ACL and PCL are intact, the accommodation space A of the bone cement applicator 500 can accommodate the tibial eminence 600 together with the ACL and PCL, while the application of bone cement B to the bone surface 200 around the tibial eminence 600 can still be carried out.

For the sake of installation of the bone cement applicator 500 on the required bone surface 200, each of the first extending portions 523 has a proximal end 523a proximal to the second opening 521 and a distal end 523b distal to the second opening 521, and perpendicular distances D1 of a top surface 523c of each of the first extending portions 523 relative to the contact surface 531 decrease gradually from the proximal end 523a towards the distal end 523b. In this way, the top surface 523c becomes sloped relative to the contact surface 531. This can effectively facilitate the installation of the bone cement applicator 500 on the required bone surface 200 without interfering with other parts of the patient's body.

In addition, to avoid the interference with other parts of the patient's body, the bone cement receiver 510 is connected with the proximal ends 523a so that there will be more room or clearance for the engagement of the bone cement supplier 400 with the bone cement receiver 510.

Figure 11:
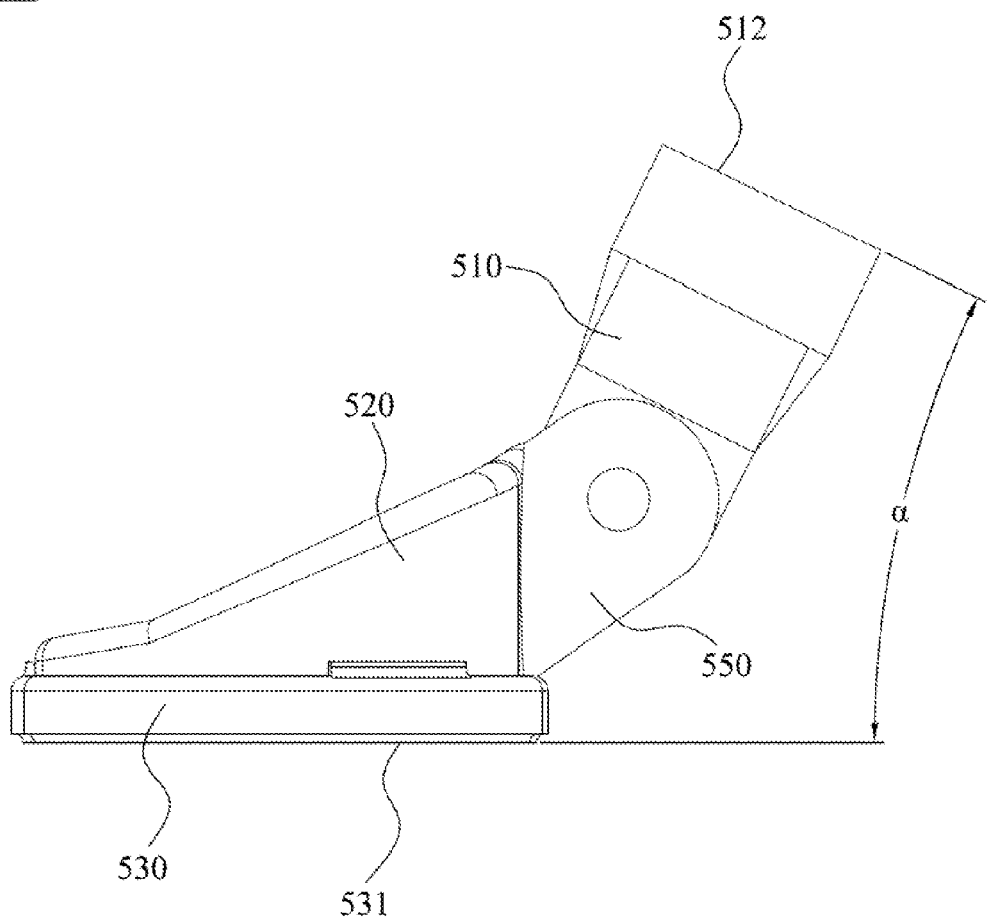
FIG. 11 is a side view of a bone cement applicator according to another embodiment of the present disclosure, in which a rotatable connector is connected with the first housing and the bone cement receiver.

FIG. 11 is a side view of a bone cement applicator 500 according to another embodiment of the present disclosure, in which a rotatable connector 550 is connected with the first housing 520 and the bone cement receiver 510. As shown in FIG. 11, the bone cement applicator 500 further includes the rotatable connector 550 connected with the first housing 520 and rotatably connected with the bone cement receiver 510. In this way, an angle α between the receiver surface 512 and the contact surface 531 of the second housing 530 can be adjusted, and the flexibility when the surgeon adjusts the orientation of the bone cement supplier 400 (shown in FIG. 1) during operation is also increased.

Figure 12:
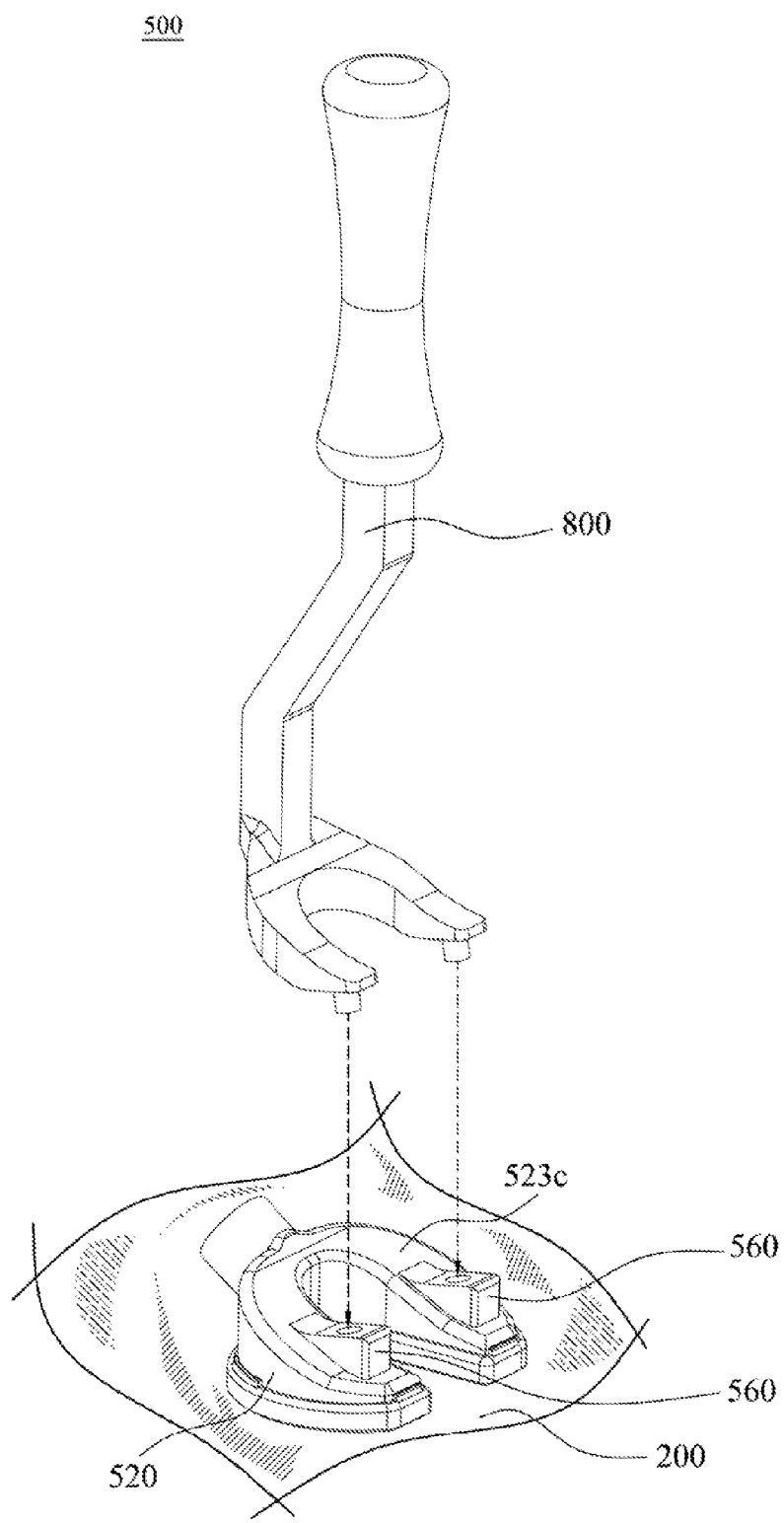
FIG. 12 is a perspective view of a bone cement applicator according to a further embodiment of the present disclosure, in which a pressing tool is ready to press on a pair of compression blocks.

FIG. 12 is a perspective view of a bone cement applicator 500 according to a further embodiment of the present disclosure, in which a pressing tool 800 is ready to press on a pair of compression blocks 560. As shown in FIG. 12, the bone cement applicator 500 further includes the pair of compression blocks 560. Each of the compression blocks 560 is located on the corresponding top surface 523c of the first housing 520. The compression blocks 560 are configured to be pressed by the pressing tool 800 in order to further secure the bone cement applicator 500 on the bone surface 200.

Figure 13:
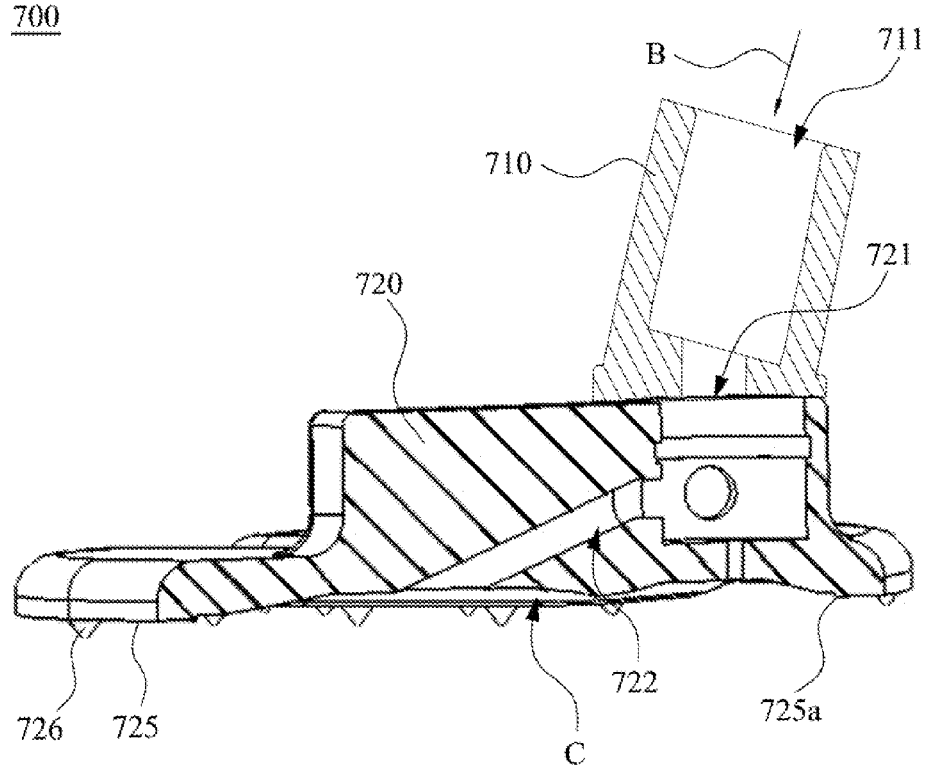
FIG. 13 is a sectional view of a bone cement applicator according to a further embodiment of the present disclosure.
Figure 14:
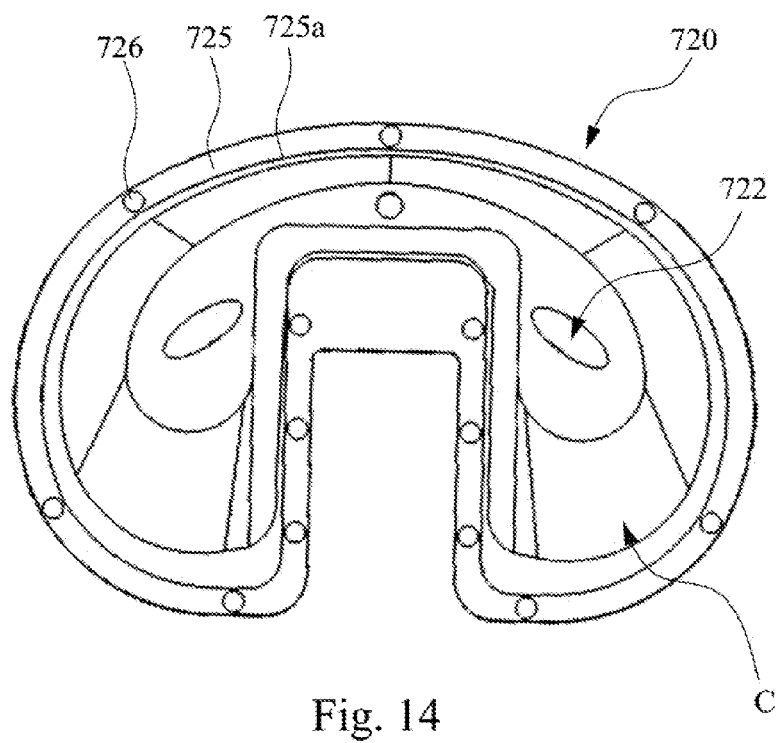
FIG. 14 is a bottom view of the bone cement applicator of FIG. 13.

FIG. 13 is a sectional view of a bone cement applicator 700 according to a further embodiment of the present disclosure. FIG. 14 is a bottom view of the bone cement applicator 700 of FIG. 13. As shown in FIGS. 13-14, the bone cement applicator 700 includes a bone cement receiver 710 and a housing 720. The bone cement receiver 710 has a first opening 711 configured to be connected with a bone cement supplier 400 (shown in FIG. 1) supplying the bone cement B. The housing 720 is connected with the bone cement receiver 710 and has a cavity C. The housing 720 includes a contact surface 725, a second opening 721 and at least one intermediate channel 722. The contact surface 725 forms a peripheral edge 725a for the cavity C in contact with the bone surface 200. In addition, the inner wall of the housing 720 adjacent to the contact surface 725 limits the flow of the bone cement B onto the bone surface 200 (with reference to FIG. 1). The second opening 721 is in fluid communication with the first opening 711. The intermediate channel 722 is in fluid communication between the second opening 721 and the cavity C, in which an orthographic projection of the intermediate channel 722 on the bone surface 200 extends away from an orthographic projection of the second opening 721 on the bone surface 200. In this way, the bone cement B can be directed by the intermediate channel 722 to a desired location other than the region of the bane surface 200 on where the orthographic projection of the second opening 721 falls.

Moreover, in this embodiment, the housing 720 further includes at least one protruding part 726 disposed on the contact surface 725 for engaging the bone surface 200. Thus, the slipping of the bone cement applicator 700 on the bone surface 200 is prevented. The protruding part 726 can be in the shape of a spike or a peg. However, the shape of the protruding part 726 does not limit the present disclosure.

Figure 15:
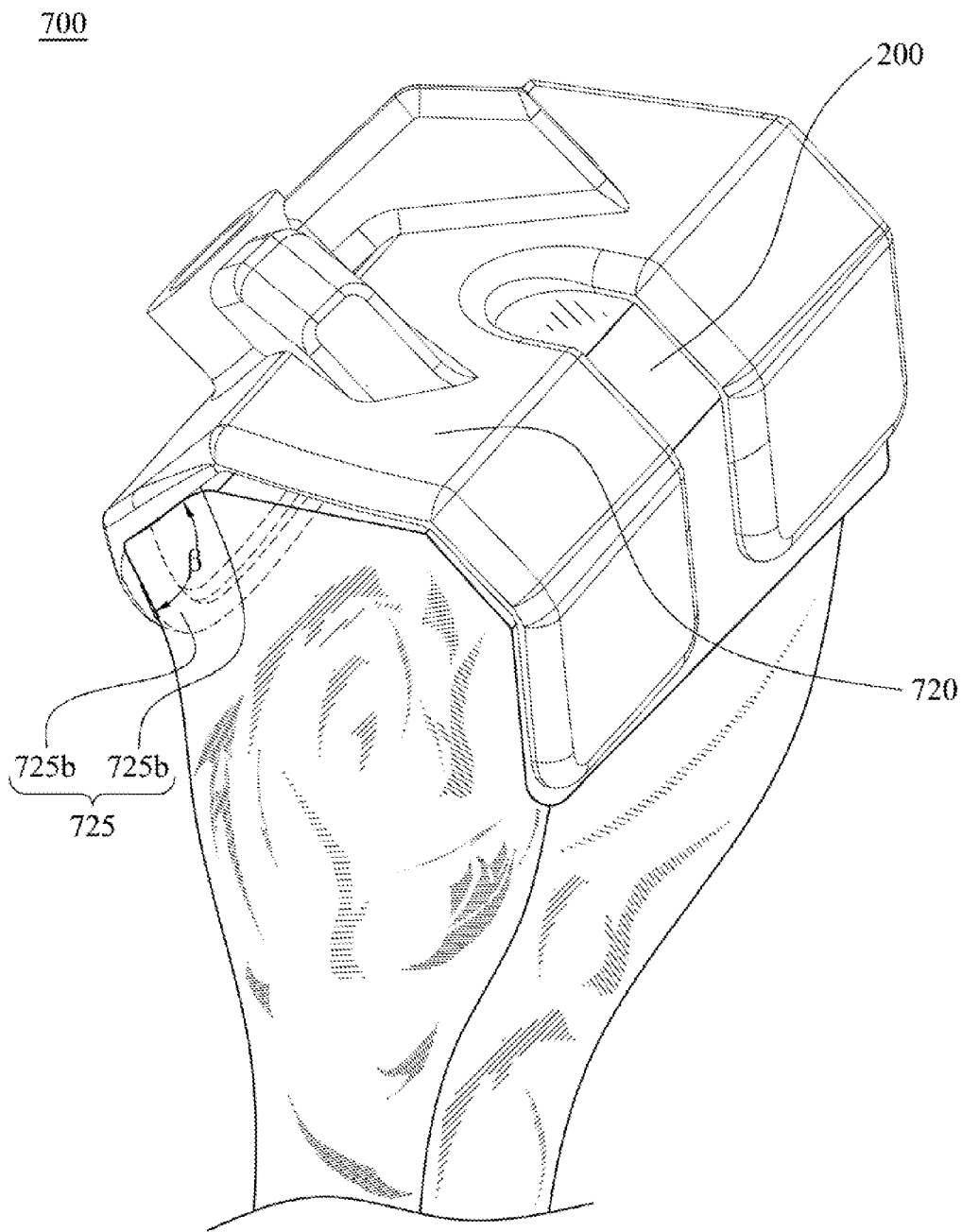
FIG. 15 is a perspective view of a bone cement applicator according to another embodiment of the present disclosure.

FIG. 15 is a perspective view of a bone cement applicator 700 according to another embodiment of the present disclosure. As shown in FIG. 15, the contact surface 725 of the housing 720 has a plurality of contact sub-surfaces 725b, and at least two adjacent ones of the contact sub-surfaces 725b form an angle β. In the embodiment, the shape of the bone cement applicator 700 can cover and fit the bone surface 200 formed in a three-dimensional pattern rather than just a flat surface.

Figure 16:
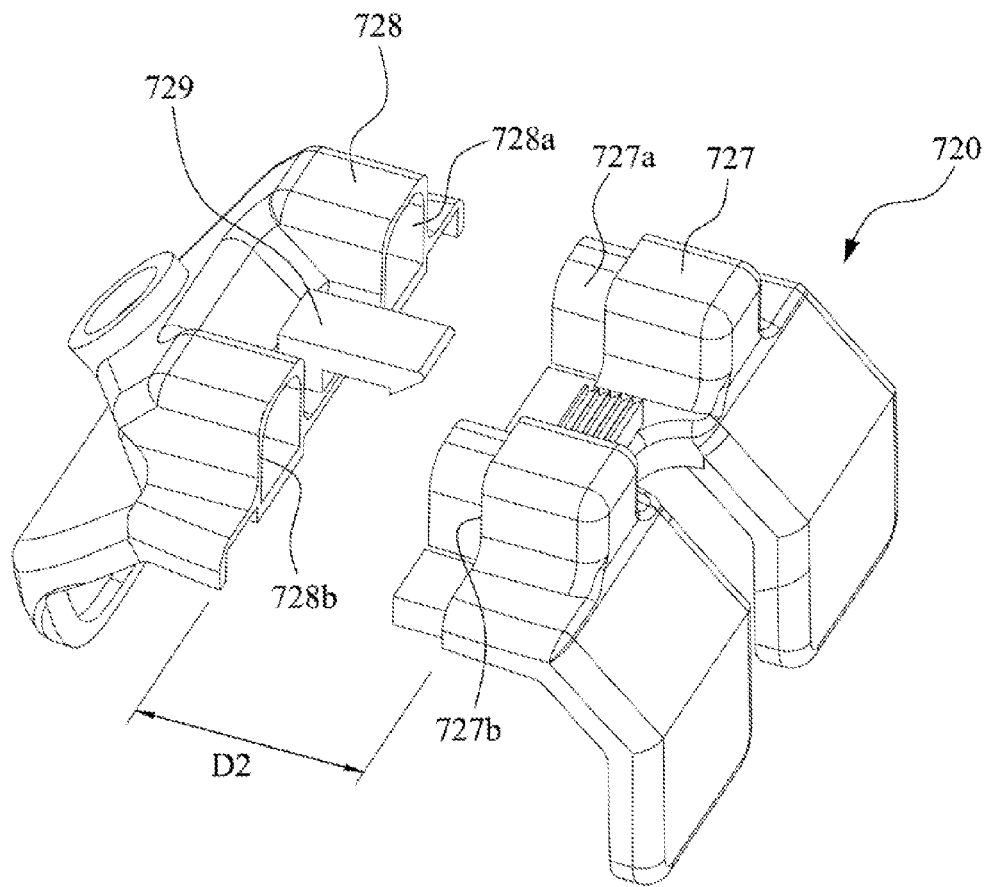
FIG. 16 is a perspective view of a bone cement applicator according to a further embodiment of the present disclosure.

FIG. 16 is a perspective view of a bone cement applicator 700 according to a further embodiment of the present disclosure. Furthermore, as shown in FIG. 16, the housing 720 includes a male portion 727 and a female portion 728. The male portion 727 has a male joint 727a. The female portion 728 has a female joint 728a. The male joint 727a is detachably engaged with the female joint 728a. In this way, the installation of the bone cement applicator 700 on the bone surface 200 (shown in FIG. 15) in a three-dimensional pattern is made simple and easy.

In addition, the male portion 727 has a male surface 727b and the female portion 728 has a female surface 728b. In this embodiment, the male joint 727a is a guiding piece and the female joint 728a is a guiding slot. The guiding piece and the guiding slot are slidably connected, such that a distance D2 between the male surface 727b and the female surface 728b can be adjusted, and thus the bone cement applicator 700 can fit different sizes of bone surface 200 in a three-dimensional pattern. The distance D2 between the male surface 727b and the female surface 728b can be fixed by an adjustable snap fit 729 as shown in FIG. 16. However, this mode of fixing does not limit the present disclosure.

In summary, when compared with the prior art, the embodiments of the present disclosure mentioned above have at least the following advantages:

(1) In the embodiments of the present disclosure, a cavity is formed between the first housing and the second housing and the bone cement reaches the bone surface after sequentially flowing through the first opening, the cavity, and the holes. In this way, the bone cement will fill up the cavity before extruding out of each of the holes and this helps to promote a more even pressurized exit of the bone cement that is being extruded. Moreover, the holes of the second housing can help spreading out the bone cement over the bone surface.

(2) In the embodiments of the present disclosure, the contact surface of the second housing includes the first zone and the second zone, and the cross-sectional area parallel with the contact surface of each of the second set of holes located in the second zone is larger than the cross-sectional area parallel with the contact surface of each of the first set of holes located in the first zone. Therefore, when the bone cement reaches the cavity, the bone cement will get accumulated in the first zone and will be spread out to the second zone. Thus, the advantage of viscosity of the bone cement is positively utilized. In this way, the effectiveness of the spreading out of the bone cement over the bone surface before passing though the holes onto the bone surface is enhanced.

(3) In the embodiments of the present disclosure, the bone cement flows onto the bone surface through the holes. In this way, the region of the bone surface receiving the bone cement is restricted by the location of the holes. Therefore, the risk that the bone cement flows to an undesired region is avoided.

(4) In the embodiments of the present disclosure, the first opening is located on the receiver surface of the bone cement receiver and the receiver surface forms an angle with the contact surface. In this way, the bone cement supplier can be connected with the bone cement receiver in an appropriate orientation convenient for the surgeon.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure.

In view of the foregoing, it is intended that the present disclosure cover modifications and variations of the present disclosure provided they fall within the scope of the following claims.

What is claimed is:
1. A bone cement applicator for applying a bone cement to a bone surface, the bone cement applicator comprising:
  a bone cement receiver having a first opening configured to be connected with a bone cement supplier supplying the bone cement;
  a first housing connected with the bone cement receiver, the first housing a separate component than the bone cement receiver; and
  a second housing connected with the first housing, the second housing a separate component than the first housing,
  a cavity being formed between the first housing and the second housing when the second housing is connected to the first housing,
  the cavity being in fluid communication with the first opening, wherein the second housing comprises:
    a contact surface in contact with the bone surface; and
    a plurality of holes located on the contact surface and in fluid communication with the cavity,
    wherein the bone cement reaches the bone surface after sequentially flowing through the first opening, the cavity, and the holes.
2. The bone cement applicator of claim 1,
  wherein the contact surface comprises a first zone and a second zone, the second zone surrounds at least a part of a peripheral edge of the first zone, the holes comprise a first set of holes and a second set of holes respectively located in the first zone and the second zone, wherein a cross-sectional areal parallel with the contact surface of each of the second set of holes is larger than a cross-sectional area parallel with the contact surface of each of the first set of holes.

3. The bone cement applicator of claim 2, wherein the first housing has a second opening in fluid communication between the first opening and the cavity, and an orthographic projection of the second opening on the contact surface at least partially overlaps with the first zone.

4. The bone cement applicator of claim 1, wherein the second housing is a porous structure.

5. The bone cement applicator of claim 1, wherein the second housing is an open-celled foam.

6. The bone cement applicator of claim 1, wherein the bone cement applicator is made of plastic.

7. The bone cement applicator of claim 1, wherein the bone cement receiver comprises a receiver surface, the first opening is located on the receiver surface and the receiver surface forms an angle with the contact surface.

8. The bone cement applicator of claim 7, wherein the first housing has a second opening in fluid communication between the first opening and the cavity, and the bone cement receiver is rotatably engaged with the second opening.

9. The bone cement applicator of claim 1, wherein the bone cement receiver comprises a threaded portion located at an inner wall of the first opening and configured to be detachable engaged with the bone cement supplier.

10. The bone cement applicator of claim 1, further comprising a ratchet clip connected to an end of the bone cement receiver away from the first housing for fastening the bone cement supplier.

11. A bone cement applicator for applying a bone cement to a bone surface, the bone cement applicator comprising:

a bone cement receiver having a first opening configured to be connected with a bone cement supplier supplying the bone cement;

a first housing connected with the bone cement receiver; and a second housing connected with the first housing, a cavity being formed between the first housing and the second housing, the cavity being in fluid communication with the first opening, wherein the second housing comprises:

a contact surface in contact with the bone surface; and a plurality of holes located on the contact surface and in fluid communication with the cavity, wherein the bone cement reaches the bone surface after sequentially flowing through the first opening, the cavity, and the holes, wherein the contact surface comprises a first zone and a second zone, the second zone surrounds at least a part of a peripheral edge of the first zone, the holes comprise a first set of holes and a second set of holes respectively located in the first zone and the second zone, and wherein a cross-sectional areal parallel with the contact surface of each of the second set of holes is larger than a cross-sectional area parallel with the contact surface of each of the first set of holes.

12. The bone cement applicator of claim 11, wherein the first housing comprises a second opening in fluid communication between the first opening and the cavity.

13. The bone cement applicator of claim 12, wherein the first housing comprises an orthographic projection of the second opening on the contact surface at least partially overlaps with the first zone.

14. The bone cement applicator of claim 11, wherein the second housing comprises a porous structure.

15. The bone cement applicator of claim 11, wherein the second housing comprises an open-celled foam.

16. The bone cement applicator of claim 11, wherein the bone cement applicator comprises a plastic.

17. The bone cement applicator of claim 11, wherein the bone cement receiver comprises a receiver surface.

18. The bone cement application of claim 17, wherein the first opening is located on the receiver surface and the receiver surface forms an angle with the contact surface.

19. The bone cement applicator of claim 18, wherein the first housing comprises a second opening in fluid communication between the first opening and the cavity.

20. The bone cement applicator of claim 19, wherein the bone cement receiver is rotatably engaged with the second opening.

21. The bone cement applicator of claim 11, wherein the bone cement receiver comprises a threaded portion located at an inner wall of the first opening and configured to be detachable engaged with the bone cement supplier.

* * * * *